United States Patent [19]

Klein et al.

[11] Patent Number: 4,730,921

[45] Date of Patent: Mar. 15, 1988

[54] PHOTODENSITOMETER FOR MINIMIZING THE REFRACTIVE EFFECTS OF A FLUID SAMPLE

[75] Inventors: Gerald L. Klein, Edmonds; Gene D. Russell, Seattle; Steven R. Day, Bothell; Jerrold D. Liebermann, Seattle, all of Wash.

[73] Assignee: Genetic Systems, Inc., Seattle, Wash.

[21] Appl. No.: 793,653

[22] Filed: Oct. 31, 1985

[51] Int. Cl.[4] .............................................. G01N 33/48
[52] U.S. Cl. .................................... 356/39; 356/440; 422/73
[58] Field of Search .......... 356/39, 244, 409, 432–436, 356/440–442; 250/573, 574, 576, 577; 422/72, 73; 435/808; 436/805

[56] References Cited

U.S. PATENT DOCUMENTS

| | | | |
|---|---|---|---|
| 2,942,515 | 6/1960 | Bernardini | 88/14 |
| 3,523,738 | 9/1970 | Chisholm | 356/201 |
| 3,883,308 | 5/1975 | Matte | 23/259 |
| 3,982,838 | 9/1976 | Thacker | 356/201 |
| 4,004,150 | 1/1977 | Natelson | 250/328 |
| 4,115,010 | 9/1978 | Mcaleer et al. | 356/201 |
| 4,201,478 | 5/1980 | Gerlier et al. | 356/440 |
| 4,240,751 | 12/1980 | Linnecke et al. | 356/409 |
| 4,254,223 | 3/1981 | Schuurs et al. | 435/296 |
| 4,299,493 | 11/1981 | Harrison | 356/414 |
| 4,367,043 | 1/1983 | Sweet et al. | 356/338 |
| 4,397,560 | 9/1983 | Andresen | 356/440 |
| 4,432,642 | 2/1984 | Tolles | 356/246 |
| 4,452,759 | 6/1984 | Takekawa | 422/73 |
| 4,465,938 | 9/1984 | Kato et al. | 250/576 |
| 4,498,780 | 2/1985 | Banno et al. | 356/414 |
| 4,498,782 | 2/1985 | Procter et al. | 356/436 |
| 4,580,895 | 4/1986 | Patel | 356/39 |

Primary Examiner—Eugene R. LaRoche
Assistant Examiner—Robert J. Pascal
Attorney, Agent, or Firm—Seed and Berry

[57] ABSTRACT

An automated vertical photo densitometer for reading solutions contained in microwell plates. The densitometer utilizes an optical system for minimizing the optical effect of a meniscus on the fluid sample. The invention also discloses a method for determining a centrally located position of a microwell beneath an interrogating beam of light by controlling the size of the light beam and by stepping the well through the beam. A measurement of the light intensity received by a detector is taken at each step. A maximum light intensity value is selected as corresponding to a well position wherein a central area of the fluid sample is substantially within the interrogating beam.

39 Claims, 11 Drawing Figures

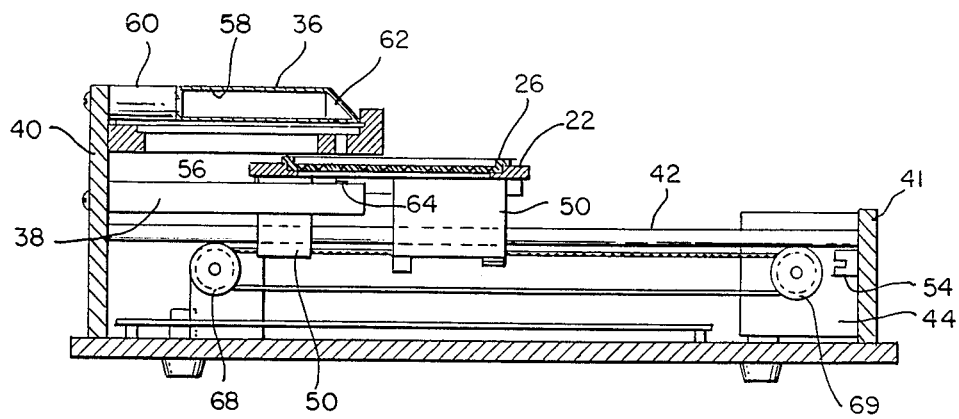
FIG. 3
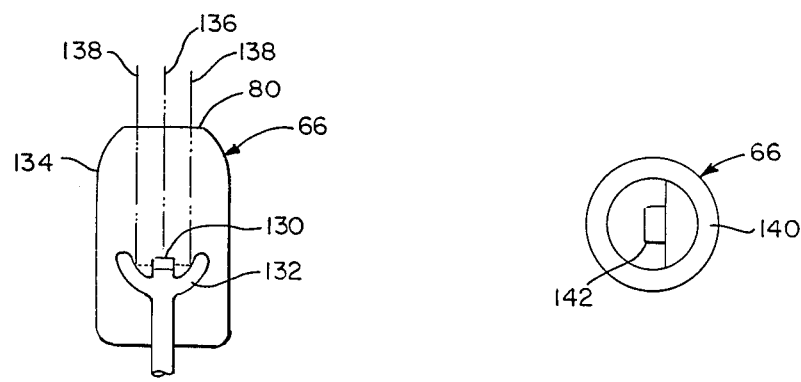
FIG. 4
FIG. 5

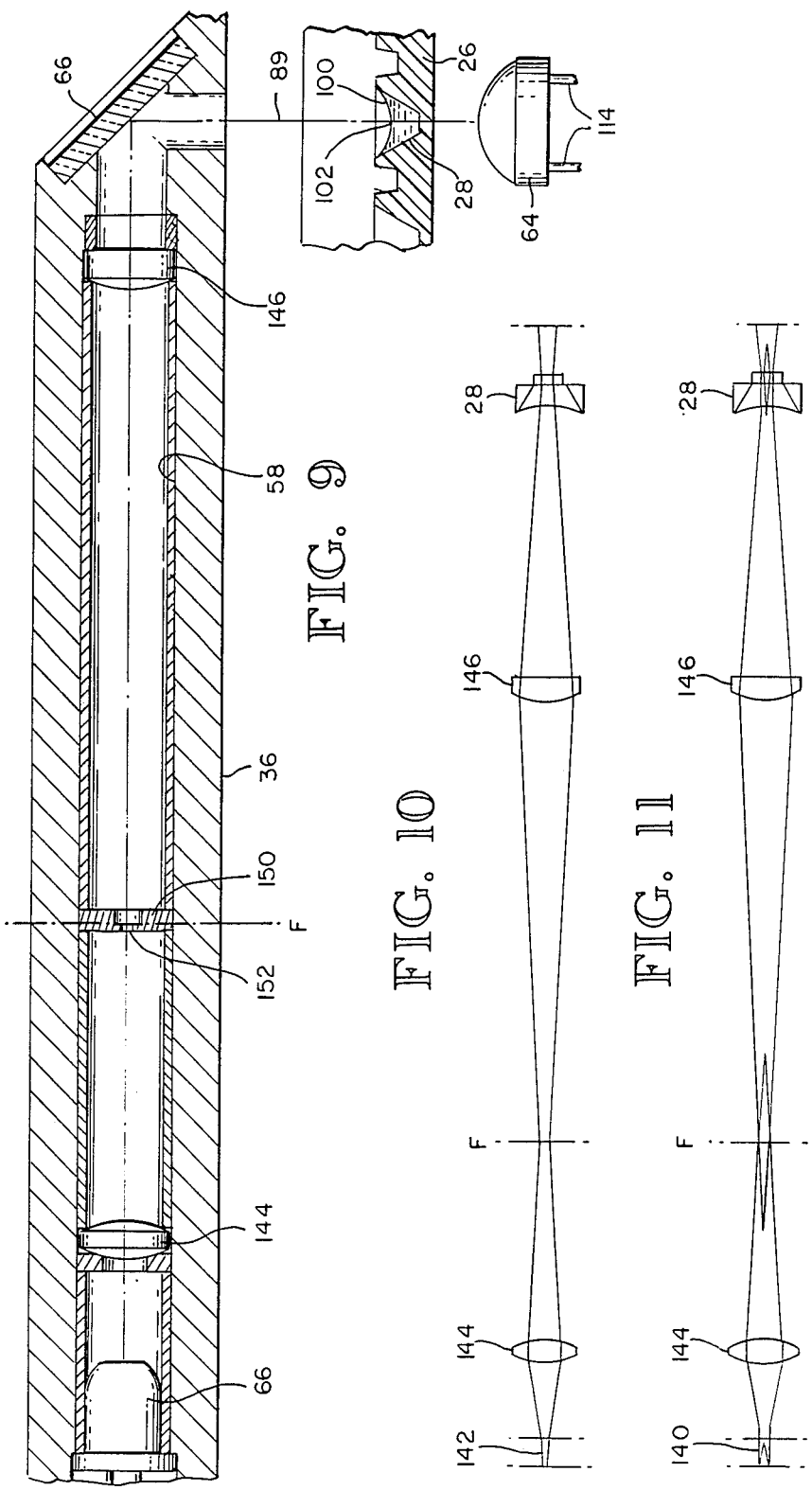

PHOTODENSITOMETER FOR MINIMIZING THE REFRACTIVE EFFECTS OF A FLUID SAMPLE

TECHNICAL FIELD

This invention relates to devices for optically measuring a characteristic of a fluid sample. More specifically, the invention relates to a method and apparatus for determining the optical density of a fluid sample using photometry.

BACKGROUND OF THE ART

In various medical and chemical tests it is often desirable to determine the occurrence of nonoccurrence of a reaction in a fluid sample. For example, in the medical field it is often highly desirable to predetermine the compatibitlity of donor tissues with host tissue prior to an organ transplant. Presently, determinations of tissue types are accomplished using cytotoxicty assays. This involves reacting cells from the donor (and in a separate determination, the host) with antisera directed against specific cell surface antigens, known as histocompatibility antigens, in the presence of a source of complement. Binding of antibody to antigen on the cell surface leads to complement-mediated lysis of the cell. If a vital dye is also present in the test medium, it is possible to distinguish live from dead cells based on their staining. Thus, it is possible to determine the repertoire of histocompatibility antigens which a particular individual's cells express. A technician visually inspects each well in the plate to determine the extent of reaction as measured by cell death. The reading and interpretation of such a plate requires about ten minutes to accomplish, depending on the number of wells in the plate and the skill of the reader.

Recent developments in molecular biology have provided new techniques in which the extent of an antigen-antibody reaction can be determined by the formation of a colored product in the fluid sample. The resulting coloration of the fluid is significantly easier to read and much less subjective than the aforementioned procedure in which cell viability is evaluated by staining with a vital dye. The new technique also gives a quantitative measure of the strength of the reaction while the previously used method yielded semi-quantitive information, at best. This improved technique affords an opportunity to automate the reading of multi-well plates by using vertical photometric density measurements. However, due to the small size and geometry of the wells within which the fluid sample is contained, a variety of problems have heretofore prevented the automation of this process.

The first problem is caused by the small diameter of the microwells presently available in microwell plates. A typical microwell in a Terasaki plate has an inverted frusto-conic shape. The bottom (narrowest) portion of the well has a substantially transparent window with a diameter of only approximately 0.047 inch. The open top (widest portion) of the well has a typical diameter of only approximately 0.16 inch. Therefore, a substantial fluid meniscus is typically formed on the top surface of the fluid sample in the well. The meniscus can vary in curvature from one well to the next thereby frustrating attempts to optically compensate for the refractive effect of the the meniscus on an interrogating light beam. The accuracy of an optical density measurement depends on providing a repeatably accurate light beam path through the fluid sample to a detector. A fundamental presumption in a density measurement of this type is that light not received at the detector end of the system is absorbed by the fluid. Stray light beams, such as caused when refracted by a meniscus, are incorrectly read by such a system as having been absorbed by the fluid. An inaccurate measurement therefore results. Attempts to predict the position and curvature of the meniscus to optically compensate for the refractive effect of the meniscus are frustrated by the variability of the meniscus curvature and position within the microwell.

A second significant problem in the automation of density measurements in microwell plates relating to the small size of the microwell is the ability to accurately place the 0.047 inch diametr well bottom directly beneath an interrogating beam of light. Typically, the plates containing the wells are mass produced in a plastic molding process. The wells are not always perfectly centered on their respective matrix positions. There is also a significant variation of the position of the matrix itself relative to the sidewalls of the plate.

A third significant problem encountered with modern microwell designs results from the irregularity of the plastic surface in the well bottom which can also refract a light beam passing therethrough.

The present invention solves the above heretofore unsolved problems in an automated system for measuring the optical density of a fluid sample in microwell plates.

DISCLOSURE OF THE INVENTION

Basically, the invention comprises a method and apparatus for minimizing the optical effect of a meniscus on a fluid sample in a vertical photometric system and for centering an interrogating light beam in each fluid well.

A light beam generated from a light source is collected and focused along an optical axis. The focused light beam defines a cone of light having a substantially reduced diameter portion. The meniscus of the fluid sample is centrally located on the optical axis. The meniscus is axially positioned substantially at the narrowest portion of the light cone so that only the central portion of the meniscus is illuminated. The diameter of the light beam at the meniscus is substantially smaller than the radius of curvature of the meniscus. Therefore, refraction of the light rays by the meniscus is minimized and variations in the degree of curvature of the meniscus have a minimal effect on the path of the light beams through the fluid sample.

In a preferred embodiment, the microwell transparent bottom is positioned substantially perpendicular to the optical axis. The light beam is focused so that the diameter of the beam at the well bottom is sufficiently small to pass entirely through the well bottom. Therefore, attenuation of the light beam is solely due to the optical density of the fluid sample. Scattering of the light beam off the wall of the microwell is substantially eliminated because of the minimized effect of the fluid meniscus and because the diameter of the light beam is small enough to entirely pass through the bottom of the well.

In order to assure that the well is positioned such that the light beam has passed with minimum refraction throught the fluid sample, a method has been devised for grossly positioning the well and for advancing the well through the beam. The well is positioned on a path radial to the optical axis of the light beam within a tolerance transverse to the radial path of one-half the diameter of a well bottom less the radius of the light beam at the well bottom. It has been found that the manufacturing variability for typical microwell plates is within this value. The well is then advanced linearly through the light beam on the radial path. As the well passes through the light beam, the intensity of light transmitted through the sample and onto a detector is measured. A maximum light intensity is measured at a radial position from the optical axis wherein the entire light beam is passing through the fluid sample and well bottom onto a detector. This measurement corresponds to a reading in which attenuation of the light beam is due solely to absorption of the beam by the fluid sample. At other positions where portions of the light beam are incident upon the sidewall of the fluid well, the intensity of light received at the detector is not a relative maximum.

In the preferred embodiment, the microwell plate containing the wells is incrementally advanced through the light beams in discrete steps. The intensity of the beam is measured at each step. The measured value of each subsequent step is compared to the measured value of a previous step. The measurement having the greater value is stored while the smaller value is discarded. After the well has been traversed in steps, the remaining stored value is a maximum value corresponding to a position wherein the entire light beam passed through the fluid sample and onto the detector and wherein attenuation of the beam is solely due to absorbance by the fluid.

In absorbence measurements of this type it is also preferred to match the intensity output of the light beam to the wavelength spectra of the fluid sample. That is, a light source is preferably chosen which as a maximum intensity output wavelength in a wavelength bandwidth which corresponds to a maximum absorption wavelength in an absorption bandwidth in the fluid sample. Where the absorbence to be measured is that of a fluid having undergone a chemical reaction, the intensity output of the lightbeam is matched to that wavelength at which the change in optical density during the chemical reaction is indicative of the degree of the chemical reaction.

BRIEF DESCRIPTION OF THE DRAWINGS

FIG. 3 is an enlarged sectional, side elevational view of the photo densitometer taken generally along line 3—3 of FIG. 2.

FIG. 4 is a schematic representation of a light emitting diode usable as a light source in the present invention.

FIG. 5 is a top plan view of the light emitting diode of FIG. 4.

FIG. 9 is an enlarged, sectional view of an alternative embodiment of an optical system for the present invention usable with the light emitting diode of FIGS. 4 and 5.

FIG. 10 is a ray diagram of the optical system of FIG. 9 illustrating the optical path of light emanating from the light emitting diode.

FIG. 11 is a ray diagram of the optical system of FIG. 10 illustrating the optical path for the halo caused by a reflector in the light emitting diode.

BEST MODE FOR CARRYING OUT THE INVENTION

Figure 1:
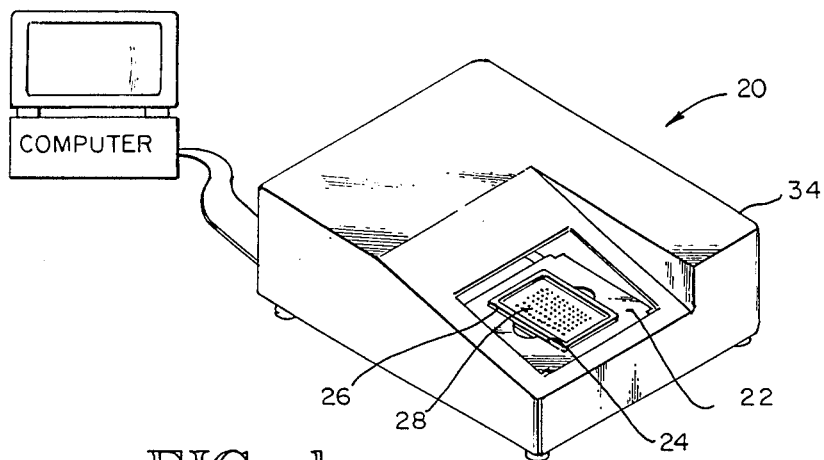
FIG. 1 is an isometric view of an automated photo densitometer for microwell plates in accordance with the present invention with the computer and display used therewith.

An automated photo densitometer, in accordance with the present invention is generally indicated by reference numeral 20. As shown in FIG. 1, the photo densitometer has a moveable carriage 22 with a receptacle 24 adapted to receive a microwell plate 26 therein. The carriage is moveable into the optical systems of the densitometer to determine the densities of the fluid samples contained in microwells arranged in an array within the plate. A computer 30 operating with the densitometer controls the operation of the densitometer and displays data obtained by the densitometer on a readout 32. The densitometer 20 is provided with an outer cover 34.

Figure 2:
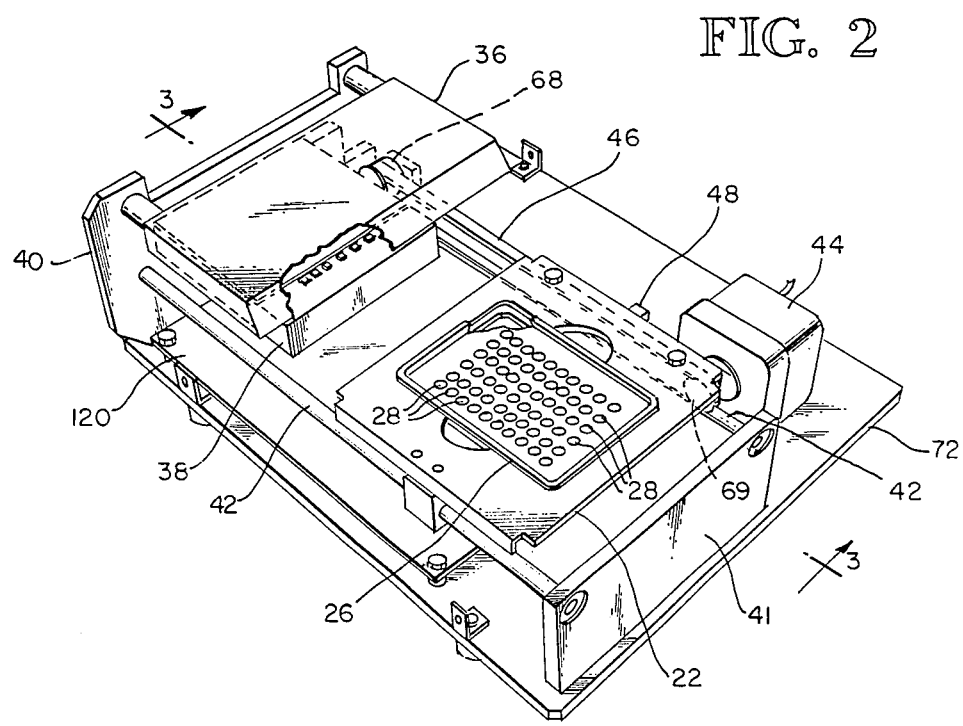
FIG. 2 is a reduced scale isometric view of the photo densitometer of FIG. 1 with the outer cover removed to illustrate various subassemblies of the invention.

In FIG. 2, the outer cover 34 of the photo densitometer 20 has been removed to reveal various subassemblies therein. A typical microwell plate 26 is also more clearly illustrated in FIG. 2. The plate has seventy-two individual microwells 28 arranged in a matrix array having six columns and twelve rows.

A stationary optical system chassis 36 supports a dedicated light source and associated optical system for each column to sequentially illuminate each well in a row of wells in the plate 26. A stationary detector array chassis 38 supports a light detector system for detecting the illumination. It is preferred to illuminate the wells sequentially to prevent cross talk. The optical system chassis 36 and detector array chassis 38 are connected to and maintained in a spaced apart relation by a frame member 40 so that the moveable carriage 22 containing the microwell plate 26 can move therebetween. The movable carriage 22 is slidably mounted on a pair of rails 42 supported at one end by the frame member 40 and at the other end by a frame member 41. A stepping motor 44 drives the carriage 22 through a belt and pulley arrangement 46 which includes a tooth drive belt 47. A variety of suitable mechanical substitutes for the belt and pulley arrangement will be readily apparent to those skilled in the art. In some prototype models a motor-driven rotary screw and follower were used to advance the carriage 22.

In the embodiment shown in FIG. 2, a clamp 48 connects the carriage 22 to the tooth drive belt 47. The stepping motor is capable of advancing the carriage in discrete steps of 0.0018 inch linear displacement. The motor is of conventional design. The drive shaft of the motor itself is capable of movement in steps of 0.9 degrees per full step. With the present invention, the motor is energized to move in half-step increments to achieve the desired linear movement of the belt.

As best shown in FIG. 3, the carriage 22 is fixedly attached to supports 50 which are slidably engaged with the rails 42. An electro-optical home detector 54 informs the computer 30 that the carriage is in a home position shown in FIGS. 1 and 6. In the home position the plate 26 may be placed in or removed from the receptacle 24 of the carriage 22.

As will be described in more detail below, the light source and optical systems of the optical system chassis 36 produces a row of 6 beams of light for sequentially illuminating the wells in a full row of 6 wells in the plate 26. The computer 30 is informed that the plate is about to enter the light beams by a leading lip 56 of the carriage 22 breaking the light beams as the carriage moves toward a position under the optical system chassis 36. The carriage 22 is shown in FIG. 3 in a reading position.

The optical system chassis 36 has six horizontal bores 58, each aligned with one column of wells in the plate. The bores 58 each contain the optical system shown in detail in FIGS. 7 and 9 which direct and focus light generated from an individual light source mounted within the optical system chassis 36. A focused beam of light generated by the light source is redirected by an angularly oriented mirror 62 positioned at one end of the bore 58 downwardly through the microwell plate 26 to a corresponding photo detector 64 within the detector array chassis 38. Six detectors 64 are provided, one for each column of wells in the plate. In the preferred embodiment, light emitting diodes (LED) 66, such as those shown in FIGS. 4 and 5, are utilized as the light source mounted in the optical system chassis 36.

Figure 6:
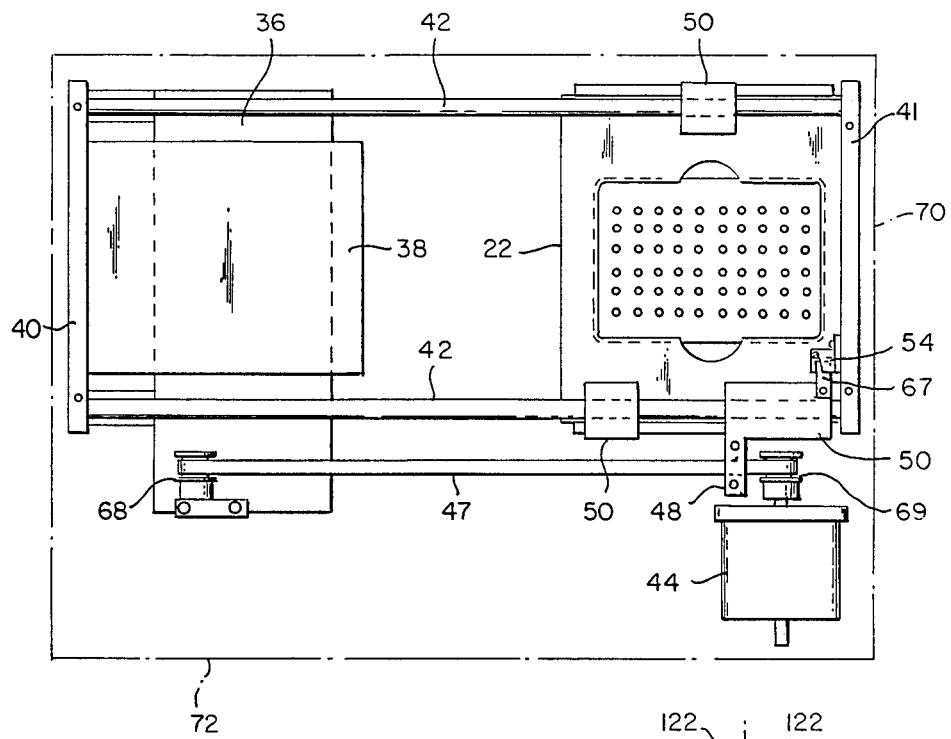
FIG. 6 is an enlarged, bottom plan view of the photo densitometer shown in FIG. 2.

FIG. 6 is a bottom plan view of the photo densitometer 20 with base 72 removed, illustrating the moveable carriage 22 in the home position. The home detector 54 is an optical detector-emitter pair which detects the presence of a tab 67 attached to the support 50 so as to be positioned therebetween when the carriage is in the home position. Those skilled in the art will recognize other suitable substitutes for the home detector shown.

The clamp 48 rigidly connects the belt 47 to one of the supports 50 to move the carriage 22 with the belt. The belt and pulley arrangement 46 includes a first pulley 68 which serves as an idler pulley, a second pulley 69 mounted on the drive shaft of the motor 44, with the belt 47 trained on the pulleys. The motor 44, first and second pulley 68 and 69, and frame members 40 and 41 are supported on a base 72.

Figure 7:
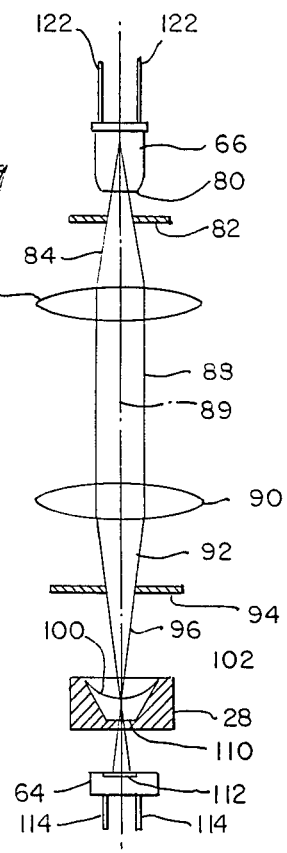
FIG. 7 is a schematic representation of one embodiment of an optical system usable in the present invention.

A first embodiment for the optical system contained in the optical system chassis 36 and for the detectors 64 contained in the detector array chassis 38 is schematically illustrated in FIG. 7. A light emitting surface 80 of the LED 66 has been gound flat to provide a controlled optical surface for the light source. A first aperture 82 is provided spaced part from the LED to define the edge 84 of the light beam entering the optical system. A collimating lens 86 is provided outward of the first aperture 82 to collect the light transmitted through the first aperture and to produce a collimated light beam 88 having an optical axis indicated by phantom line 89. A focusing lens 90 is positioned outward of the collimating lens 86 to produce a cone of light 92 having its edge defined by a second aperture 94 and to provide a well defined cone of light 96.

The microwell 28 is axially positioned relative to the optical system so as to be on the optical axis 89. In such manner, a concave fluid meniscus 100 formed by the fluid sample in the well has a central portion 102, with a diameter approximatley equal to the well bottom diameter, which is oriented substantially perpendicular to the light beam 96 at the intersection thereof. Therefore, refraction of the light beam due to the curvature of the fluid meniscus is substantially minimized. It is well known that a light beam incident upon a surface interface between two media having different refraction indices will be only slightly refracted if the angle of the incidence is small when measured from a normal line to the surface. Stated otherwise, it is highly preferred to place a central area of the meniscus in the path of light cone at the position where the cone has its minimum diameter (narrowest beam width) to minimize refraction of the light beam according to Snell's law. This effect can be achieved if the diameter of the beam is small compared to the radius of the curvature of the meniscus. Since, however, it is also desirable to position a substantially transparent bottom 110 of the microwell being illuminated at the position where the narrowest beam width of the light beam occurs, so that the diameter of the light beam at the bottom of the well is small compared to the well bottom diameter, a compromise must be made. It is noted that if the diameter of the light beam at the bottom of the well is too large, light is reflected off the interior walls of the well and the density reading will be erroneous. In one embodiment, the focusing lens 90 is positioned to focys the collimated light beam 88 so that the cone of light 96 has an image of the light source LED 66 approximately at the intersection of the light beam and the fluid meniscus 100. In general, the above parameters can be satisfied by providing a focused beam, having a small diameter compared to the curvature of the fluid meniscus at their point of intersection, while also providing a relatively small diameter light beam that exits through the bottom 110 of the microwell 28.

The detector 64 is positioned to be sufficiently close to the transparent bottom 110 of the microwell to receive substantially all of the light transmitted therethrough. The detector has a light sensitive surface 112 which is larger in area than the diameter of the beam where it impinges on the detector surface. The detector generates an electrical signal responsive to the intensity of light received by the detector. A pair of detector leads 114 transmit the electrical signal to a printed cirucuit board (not shown) mounted to the detector array chassis 38, which in turn transmits the signal to a printed circuit board 120.

The printed circuit board 120 positioned within the photo densitometer 20 contains electrical circuits (not shown) for conditioning the signal received from each of the detectors 64, for driving the stepper motor 44, and for generating the electrical signals used to energize the LEDs 66 through a pair of light source leads 122. The circuit may contain analog-to-digital converters and digital-to-analog converters to allow communication between the computer 30 and the densitometer 20.

FIGS. 9, 10 and 11 illustrate a second embodiment of the optical system which is contained in the bores 58 of the optical s ystem chassis 36 to produce a light beam of the desired dimensions using light emitting diodes of the type shown in FIGS. 4 and 5. It is highly desirable to utilize a light source which has a maximum output intensity at a frequency (wavelength) which corresponds to an absorption frequency (wavelength) maximum at which the change in optical density during the chemical reaction is indicative of the degree of the chemical reaction. Some commercially available light emitting diodes have a majority of their light output in a half power wavelength bandwidth of approximately 40 nanometers. For certain applications, such as absorption measurements of colorimetric assays using the chromagen OPD, the preferred wavelength bandwidth is centered at approximately 660 nanometers.

A diode of this type is schematically illustrated in cross-section in FIG. 4. The diode 66 has a diode element 130 supported on a spherical or parabolic reflector 132. Some of the light generated by the diode element 130 is directly transmitted through a diode housing 134 and is indicated by the phantom line 136. Another portion of the light generated by the diode element is reflected off the reflector 132 and transmitted through the housing 134, as indicated by the phantom line 138.

FIG. 5 shows a top plan view of the light pattern emitted by the diode 66 of FIG. 4. The light rays traveling a path along line 138 form an annular halo 140 which surrounds an image 142 of the diode element 130. As previously discussed, it is highly desirable to focus a very narrow beam of light onto the central portion 102 of the fluid meniscus 100 in the well 28. A focused image produced by the diode shown in FIGS. 4 and 5, however, will not be a point source. Rather, it is a small central image of the diode element 142 surrounded by the annular halo 140. The halo is difficult to reduce in size without causing other undesirable secondary optical effects.

The optical system shown in FIG. 9 has an intermediate aperture 150, which is not present in the optical system of FIG. 7, and a different optical arrangement which eliminates the halo.

FIG. 10 illustrates a ray diagram of the directly transmitted portion 136 of the diode element 130 indicated by image 142 in FIG. 5. The collimating lens 86 of FIG. 7 has been replaced by a first focusing lens 144 to focus the image 142 of the diode element 130 at a plane designated by the reference character "F".

FIG. 11 is a ray diagram of the halo 140 shown in FIG. 5. The image of the annular halo is also focused at the plane F. It is noted that the inner diameter of the halo shown in FIG. 11 at plane F is larger than the diameter of the diode element image 142 at plane F. The intermediate aperture 150 is placed at the plane F and has a central opening 152 sized to allow the focused diode element image 142 to pass therethrough and to block the halo image 140 thereat. Thus, the image of the light source incident at the central portion 102 of the fluid meniscus 110 more closely resembles a point source. A focusing lens 146 performs the same function as the focusing lens 90 of FIG. 7.

In a third embodiment (not shown) for the optical system contained in the bores 58, the length of the optical path defined by the optical axis is increased and only a single focusing lens is used.

Those skilled in the art will readily recognize other methods for decreasing the diameter of the light beam at the fluid meniscus after reviewing the above description and corresponding figures.

Figure 8:
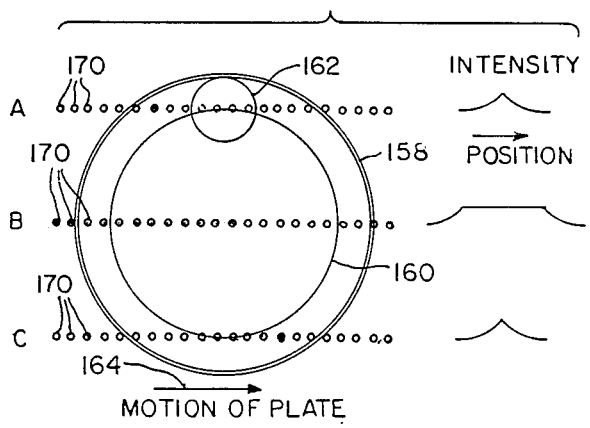
FIG. 8 is a schematic representation of the microstepping method of the present invention.

FIG. 8 is a diagramatic representation illustratng a preferred method for measuring the intensity of light transmitted through the microwell at a position displaced from the optical axis wherein the optical path of the light beam is entirely directed through the well bottom 110. Generally, the microwell 28 is advanced through the light beam 96 in discrete steps. A measurement of the light intensity received by the detector is made at each step. The method for determining a value density measurement is described below.

The outermost circle 158 represents the circumference of the well bottom 110. The concentric inner circle 160 represents the boundary of a geometric area defined by the centers of the light beam (represented by circel 162) wherein if the center of the light beam 162 is on or within the circle 160, the entire light beam is within the well bottom 158. Due to manufacturing variances in the placement of the well matrix on the plate, and the placement of the wells within each column of the matrix, the well may be transversely positioned relative to the optical axis of the light beam as the well is stepwise moved through the beam. Although it is undesirable to have the light beam impinge upon the sidewall of the well, and the reading of the intensity should be taken with the light beam passing entirely through the bottom of the well, it is not possible due to the manufacturing variances to so position the well with a simple and inexpensive mechanical system.

The preferred method allows the light beam to be transversely misaligned with a central path through the well with certain tolerances as the well is moved therethrough, yet still produce an accurate reading o intensity.

Tracks A and C represent the maximun lateral position which the center of the light beam 162 generated for the column of the wells can have relative to a central path B extending diametrically through the center of the well, as the plate moves through the beam in the direction indicated by arrow 164. Any track for the beam center between tracks A and C guarantees that at some point along the track the light beam 162 will be entirely within the well bottom 110 indicated by circle 158. Stated differently, whenever the center of the light beam 162 is on or within the area defined by the inner circle 160, attenuation of the light beam is due to absorbance by the fluid sample and is not due to scattering of the beam off the sidewall of the well 28.

The plurality of points 10 forming the tracks represent incremental positions for the center of the beam 162 as the motor 44 increments the drive belt 47 to stepwise move the microwells through the beam as the beam scans the column of wells. At each incremental position, the intensity of the light beam received by the detector 64 is measured. A plot of typical light intensities measured for the maximum transverse positions of the beam indicated by tracks A and C, and also for the central position of the beam indicated by track B are illustrated at the right-hand side of FIG. 8. In each intensity diagram it can be seen that no matter what the transverse position of the light beam, a maximum intensity value is received when the entire light beam 162 is within the well bottom 110 indicated by circle 158. The computer 30 selects a maximum value for the track that the light beam has scanned as the value corresponding to a valid density reading for the well.

Any variety of numerical methods can be employed by the computer to select such a maximum. In the preferred embodiment, one method utilized is to compare the intensity measurement taken at each subsequent step to the intensity measurement taken at the previous step. If the intensity measurement of the subsequent step is larger than the measurement of the previous step, the value of the subsequent step is stored and the previous value is discarded. This process of comparison is repeated at each step until the end of the well has been traversed. The computer can be programmed to control the motor and drive the movable carriage 22 across the light beam by counting the number of steps taken and by knowning the dimensions of a step increment and the diameter of a well. For example, if the well diameter at the top of the well is 0.16 inch and each step increment is 0.0018 inch then 25 steps will need to be taken to cross a well. At this point, the computer can instruct the stepping motor 44 to quickly move to the next well to be scanned by knowning the average distance between wells.

It will be readily apparent to those skilled in the art that various other methods for selecting a maximum intensity value can be substituted for that described above. For example, the computer could remember each value measured for a well and then utilize a sorting routine to select the maximum value.

It will be appreciated that if the light beam scans along track B or any other intermediate tracks between tracks A and C, a plateau of maximum values is achieved once the entire light beam 162 has crossed into the well bottom 110. The above-described comparison method selects the first maximum value as a reading corresponding to a position of the light beam 162 within the well bottom 110. Therefore, multiple maxima do not cause erroneous readings.

The distance between tracks A and B and tracks B and C is larger than the manufacturing variance of the placement of microwells 28 within the microwell plate matrix and the placement of the matrix relative to the external walls of the microwell plate 26. By grossly positioning the columns of microwells 28 in substantial radial alignment to the optical axes of the respective optical systems, the well columns will pass beneath the optical axes somewhere between tracks A and C as illustrated in FIG. 8. Within these tolerances, a reliable reading can be substantially assured. It will be appreciated that the tolerance within which the center line of the well columns must be transversely aligned with a radius of the optical axis is equal to the distance between tracks A and B or tracks B and C. This tolerance is equal to a well radius less the radius of the light beam at the well bottom. Therefore, the diameter of the beam must be sufficiently small so that transverse misalignment of the beam path with a central path through the well does not prevent the beam from entirely penetrating the well at some point on the misaligned path.

As noted above, it is very desirable to predetermine the compatibility of donor tissue with host tissue prior to an organt transplant. Since response to HLA antigens dominate the immunological reaction to transplanted tissue it is desirable to match donor HLA type to the recipient HLA type, thereby avoiding rejection. The preferred apparatus and method of the present invention are particularly adept in determining donor/host HLA compatability when utilized with the technique described below. In addition, determination of HLA type could be used in paternity testing.

The HLA type of an individual is determined by antigens encoded by genes on a single chromosone. Four principle HLA antigen loci have been identified on chromosome six and have been designated A, B, C and D (and the closely related DR and DO loci). A particularly advantageous application of the present invention, then, resides in an expedient method of determining HLA types.

One such assay may be generally described as follows:

Microtray wells are coated with peptide, e.g., poly-L-lysine by incubating in a solution of the peptide at a moderately elevated temperature (30°–50° C.) for about 0.1 to 2 hours, the solution decanted and the wells washed. Human leukocytes are introduced into the wells, the trays centrifuged and a dilute buffered protein solution, e.g., 1% BSA, added and the trays stored in a cold room, e.g., 4° C. for from 1 to 48 hours. The plates are then thoroughly washed.

In a mode referred to as indirect, monoclonal antibody to the antigen is added, the mixtures incubated, followed by thorough washing to remove nonspecifically bound antibody. Antibody to the monoclonal antibody (anti IgX, where X is usually M or G), particularly as $F(ab')_2$ conjugated to ane enzyme label is added followed by incubation at ambient temperatures. Usually, 0.2 to 2 hr incubation will suffice. For the direct assay, the monoclonal antibody is conjugated to the enzyme label, avoiding the addition of the anti-IgX. The labeled antibodies are employed at appropriate concentrations in an appropriately buffered medium with a blocking agent, e.g., 0.1% BSA in PBS.

The antibodies may be grouped into panels depending upon the purpoe of histocompatibility typing. In paternity testing, for isntance, a panel of 25–30 monoclonal antibodies covering the HLA-A and -B alleles would enable one to exclude paternity with a certainty of greater than 90% (see, for example, *Family Law Quarterly*, 10:3, 1976; Jeannet et al. *Vox Sang* 23:197,1972). For transplantation, panels of antisera would be used to type for both class I (HLA-A,B) and class II (HLA-DR,DQ).

More specifically, a microenzyme-linked immunosorbent assay (ELISA) may be used to detect monoclonal antibody binding to HLA antigens. This assay may be used in a direct or an indirect mode with known monoclonal antibodies to determine the HLA type of human cells, and would be performed as follows:

Terasaki microtrays are prepared by addition to each well of 5 $\mu$l of a lug/ml solution of poly-L-lysine in phosphate buffered saline (PBS). The plates are incubated at 37° C. for one hour and washed with PBS by immersion and decanting. Human Leukocytes are dispensed into each well, 1 $\mu$l of a suspension of 1 to $5 \times 10^6$ cells per ml of RPMI-1640 medium without serum. The plates are centrifuged at 90 g for three minutes. A solution of 1% bovine serum albumin (BSA) in PBS with 0.2% azide is added to the plates which are stored at 4° C. for 1 to 48 hours. Before adding antibody, the plates are washed three times.

In the indirect assay, monoclonal antibody is added, 1 $\mu$l per well. After one hour at room temperature, the plates are washed five times and a solution of the $F(ab')_2$ fragment of anti-immunoglobulin coupled with horseradish peroxidase (HRP) is added, 5 $\mu$l per well. The plates are then incubated at room temperatue for 30 to 60 minutes. In the direct assay, HRP is coupled to the monoclonal antibody, the second step is thus unnecessary. Antibodies coupled to HRP are diluted in a solution of 0.1% BSA in PBS without azide.

After treatment with antibody, the trays are washed five times. the presence of HRP-antibody complexes in the wells is visualized by the addition of a soultion of substrate, hydrogen peroxide, and chromagen, OPD (organon Diagnostics, West Orange, N.J.) or ABTS (Boehringer-Mannheim Biochemicals, Indianapolis, Ind.) in 0.1M sodium citrate/0.2M sodium phosphate. Color change in wells after 30 to 60 minutes incubation at room temperature indicates binding of monoclonal antibody to leukocytes in those wells.

The color change acting as a relative measure of the strength of the reaction in the well results in a fluid sample having an absorption maxima at a specific wavelength wherein the optical density of the fluid sample at this wavelength is proportional to the degree of the reaction, in this case the formation of antigen/antibody complexes.

Assays, incorporating the above-described technique, can be prepared for use in the microwell plate 26. Density measurements, indicating the degree of reaction occurring in each microwell 28, are reported by the computer readout 32 to an operator.

It will also be appreciated that other embodiments and variations of the invention as disclosed are contemplated. For example, the method disclosed for minimizing the optical effect of the meniscus in a fluid sample can be applied to measurements other than density readings including but not limited to optical fluorescence and optical density distributions. Therefore, the scope of the invention is not to be limited to the above description but is to be determined by the claims which follow.

We claim:

1. A photometric method for minimizng the optical effect of a meniscus on a fluid sample, comprising the following steps:
   generating light from a light source;
   collecting the generated light and forming a light beam having a central optical axis;
   focusing the light beam to form a vertical cone of light; and
   axially positioning the meniscus of a fluid sample substantially at the narrowest portion of the light cone so that a central portion of the meniscus illuminated by the light cone has a minimal refractive effect on the light beam.

2. The method of claim 1 wherein the narrowest portion of the light cone has a diameter which is substantially smaller than the radius of curvature of the meniscus.

3. The method of claim 1 wherein the fluid sample is contained in a fluid well having an open top and a substantially transparent bottom and wherein the well bottom is substantially perpendicular to the optical axis, and further including the step of positioning a light detector beneath the well bottom to receive substantially all of the non-absorbed light transmitted through the fluid sample.

4. The method of claim 3 wherein the light beam is focused such that the diameter of the light beam at the well bottom is sufficiently small to pass entirely through the well bottom.

5. The method of claim 4 wherein the detector has a detecting surface which is larger than the area of the light beam incident upon the detecting surface through the well bottom.

6. The method of claim 3 wherein the light beam is focused such that the image of the light source is axially positioned substantially at the axial position of the meniscus.

7. The method of claim 1 wherein the fluid sample has an optical density maxima at a certain wave length and wherein the light source has a maximum output intensity at a wavelength which substantially approximates the fluid sample optical density maxima.

8. The method of claim 7 wherein the fluid sample has an optical density change at a certain optical density change wavelength during a chemical reaction that is indicative of a degree of the reaction and wherein the light source has a maximum output intensity at a wavelength which substantially approximates the optical density change wavelength of the fluid sample that is indicative of the degree of chemical reaction.

9. The method of claim 8 wherein the wavelength of the light source has a maximum output intensity at approximately 660 nanometers.

10. The method of claim 7 wherein the wavelength bandwidth of the light source maximum output intensity is less than approximately 40 nanometers.

11. The method of claim 7 wherein the light source is a light emitting diode.

12. The method of claim 11 wherein the light emitting diode has a substantially planar front surface aligned substantially perpendicular to the optical axis.

13. The method of claim 3 including the following steps:
   grossly positioning the fluid well transverse to a radial path of the optical axis within a predetermined tolerance;
   moving the fluid well and the light beam relative to one another along the radial path so that the light beam then transverses at least a portion of the well bottom and so that at some point on the path substantially all of the light beam entering the fluid at the meniscus passes the well bottom to the detector;
   measuring the intensity of the light beam received by the detector as the beam and well move relative to each other; and
   selecting the measurement having a maximum value as indicative of a measurement corresponding to a position wherein the entire light beam has passed through the well bottom.

14. The method of claim 13 wherein the predetermined tolerance for the gross positioning transverse to the radial path is smaller than one-half of a well bottom transverse dimension less the radius of the light beam at the well bottom.

15. The method of claim 13 wherein the step of transversely moving the light beam and the fluid well relative to one another is achieved by incrementally moving the well through the light beam in discrete steps and wherein the step of measuring the intensity of the light beam is achieved by measuring the intensity at each discrete step.

16. The method of claim 13 wherein the step of selecting the measurement having a maximum value is achieved by comparing a previously measured intensity value at a previous step to a subsequently measured intensity value at a subsequent step and storing the greater of the two values and discarding the smaller at each step wherein the stored value is always the greatest value of any preceding measurement taken at any preceding step so that the stored value at a step corresponding to the last measurement of a well is a maximum intensity value received by the detector.

17. A vertical photometer for measuring an optical characteristic of a fluid sample having a meniscus and for minimizing the optical effect of the meniscus, comprising:
   a light source;
   means for collecting light from the light source to form a light beam defining an optical axis;
   means for positioning a central portion of a meniscus on a fluid sample substantially perpendicular to the optical axis; and
   means for focusing the light beam to define a cone of light having a reduced diameter portion at the central portion of the meniscus so that refraction of the beam by the meniscus is minimized.

18. The photometer of claim 17, including a light detector positioned on the optical axis and spaced sufficiently from the reduced diameter portion of the light cone to allow a fluid sample to be placed therebetween and wherein the detector has a light detecting surface larger than the area of the light beam incident upon the detector surface.

19. The photometer of claim 17 including a light detector positioned on the optical axis behind the optical image of the light source to receive substantially all of the light beam and to provide a space adapted to receive a well containing the fluid sample between the focusing means and the detector.

20. The photometer of claim 19 wherein the focusing means causes the light beam to have a diameter at the axial position of the detector which is substantially less than the area of the detector.

21. The photometer of claim 20 wherein the fluid sample positioning means is a movable well carriage having a well receptacle adapted to receive a well having an open top and a substantially transparent bottom for containing the fluid sample and wherein the carriage is positionable to place a well in the receptacle between the focusing means and the detector and the photometer, also including means for moving the well carriage on a path radial to the optical axis for moving the well through the light beam.

22. The photometer of claim 21 wherein the well carriage moving means grossly positions a well received therein within a predetermined tolerance transverse to the radial path.

23. The photometer of claim 22 wherein the carriage receptacle is adapted to receive a microwell plate having a plurality of wells disposed in an array of rows and columns and wherein the radial path transverse gross positioning tolerance is approximately one-half of a well bottom diameter less the radius of the light beam at the well bottom.

24. The photometer of claim 23 wherein the well carriage moving means moves the wells through the light beam in discrete incremental steps, wherein the increments are smaller than the diameter of a well bottom.

25. The photometer of claim 24 including means for measuring the intensity of light received by the detector at each step and for selecting a maximum intensity value to indicate a measurement wherein the optical path of the light beam incident on the meniscus completely exits the fluid through the well bottom.

26. The photometer of claim 21 including means for measuring the intensity of light received by the detector and for selecting a maximum measured intensity value to indicate a measurement wherein the optical path of the light beam incident upon the fluid meniscus is completely intercepted by the detector.

27. The photometer of claim 21 wherein the well carriage moving means moves the well carriage on the radial path in discrete increments wherein the increments are smaller than a dimension of a well bottom.

28. The photometer of claim 17 wherein the light source has a maximum output at a wavelength substantially approximating the wavelength of an absorption maxima of the fluid sample.

29. The photometer of claim 28 wherein the light source maximum output intensity is in a bandwidth of approximately 40 nanometers.

30. The photometer of claim 17 wherein the light source is a light emitting diode of the semiconductor type.

31. The photometer of claim 30 wherein the diode is encased in a light transmissive material having a substantially planar surface substantially perpendicularly aligned with the optical axis.

32. A photometric method for substantially locating a vertical light beam within a central portion of a fluid well bottom wherein the fluid well has a coordinate position on a plate having a known manufacturing variance, comprising the following steps:
   selecting a beam diameter at the well bottom smaller than the well bottom diameter;
   grossly positioning the plate so that the center of the well is positioned transverse to a radial path through the axis of the light beam within a predetermined tolerance which is smaller than the well bottom radius less the beam radius;
   using a plate having a manufacturing variance for the coordinate position of the well which is less than the predetermined tolerance; and
   moving the beam and plate relative to one another along a parallel path to the radial path and within the predetermined tolerance so that all of the beam passes through the well bottom at some point on the parallel path.

33. The method of claim 32 including the following steps:
   measuring the intensity of light transmitted through the well bottom as the beam and well are moved relative to one another;
   detecting a maximum intensity measurement; and
   associating the detected maximum with a beam position wherein all of the beam has passed through the well bottom.

34. A photometric method for measuring the optical density of a fluid sample, comprising the following steps:
   containing the fluid sample in a fluid well having an open top and a substantially transparent bottom;
   forming a light beam having a central optical axis;
   focusing the light beam to provide a substantially narrowed portion thereof;
   grossly positioning the center of the well transverse to a radial path through the optical axis within a predetermined tolerance;
   axially positioning the well in a radial plane such that a central portion of a fluid meniscus on the fluid sample can be illuminated by the substantially narrowed portion of the focused beam to minimize refraction of the beam by the meniscus; and
   moving the beam and well relative to one another along a parallel path to the radial path in discrete steps so that all of the beam passes through the well bottom at some point on the parallel path.

35. The method of claim 34 including the following steps:
   measuring the intensity of light transmitted through the well bottom as the beam and well are moved relative to one another;
   detecting a maximum intensity measurement; and
   associating the detected maximum with a beam position wherein all of the beam has passed through the well bottom.

36. A method for determining a central location of a light beam within a well having upwardly projecting sidewalls and a substantially flat, transparent portion, comprising the following steps:

moving the light beam and the well relative to one another along a path such that all of the beam passes through the transparent portion at some point on the path;

measuring the intensity of the light transmitted through the substantially transparent portion;

detecting a maximum intensity measurement; and associating the detected maximum with a central beam location wherein all of the beam has passed through the substantially transparent portion.

37. The method of claim 36 wherein the light beam and transparent portion are moved relative to one another in discrete steps.

38. The method of claim 37 wherein the step of detecting a maximum intensity measurement is achieved by comparing a previously measured intensity value at a previous step to a subsequently measured intensity value at a subsequent step and storing the greater of the two values and discarding the smaller at each step, wherein the stored value is always the greatest value of any preceding measurement taken at any preceding step so that the stored value at a step corresponding to the last measurement of a well is a maximum intensity value received by the detector.

39. A method for determining the HLA type of cells, comrprising the following steps:

introducing a human leukocyte suspension into a plurality of wells having open tops and substantially transparent bottom portions wherein the wells are coated to enhance the binding of the leukocytes to the wells;

centrifuging the cell-containing wells thereby forming supernatant;

removing the supernatant and washing the cell-containing wells;

adding monoclonal antibody specific for an alloantigen into at least one well, wherein differing monoclonal antibodies are put in different wells resulting in the formation of monoclonal antibody/cell complexes;

washing the wells to remove nonspecifically bound monoclonal antibody;

adding antibody conjugated with an enzyme or a receptor conjugated to an enzyme which binds to the monoclonal antibody/cell complexes;

adding a colorimetric substrate to the wells to provide a fluid sample having an absorption maxima at a specific wavelength, wherein the optical density of the fluid sample at the wavelength is proprotional to the degree of formation of antigen-antibody complexes;

generating a light from a light source substantially at the wavelength;

collecting the generated light and forming a light beam havng a central optical axis;

focusing the light beam to form a vertical cone of light;

axially positioning the meniscus of the fluid sample substantially at the narrowest portion of the light cone so that a central portion of the meniscus illuminated by the light cone has a minimal refractive effect on the light beam;

moving the light beam and the transparent portion relative to one another along a path such that all of the beam passes through the transparent portion at some point on the path;

measuring the intensity of the light transmitted through the substantially transparent portion; and detecting the light transmitted through the fluid sample and therefrom determining the HLA types of the cells.

* * * * *

UNITED STATES PATENT AND TRADEMARK OFFICE
CERTIFICATE OF CORRECTION

PATENT NO. : 4,730,921

DATED : March 15, 1988

INVENTOR(S) : Gerald L. Klein; Gene D. Russell; Steven R. Day
Jerrold D. Liebermann It is certified that error appears in the above—identified patent and that said Letters Patent is hereby corrected as shown below:

In Claim 13, line 11, add the word --through-- following "passes", and before "the".

In Claim 39, the 2nd to last line, delete "types" and substitute therefor --type--.

Signed and Sealed this

Twenty-third Day of August, 1988

Attest:

DONALD J. QUIGG

*Attesting Officer*  *Commissioner of Patents and Trademarks*